United States Patent
Rhemrev-Pieters (10) Patent No.: US 11,974,777 B2
(45) Date of Patent: *May 7, 2024

(54) TISSUE RECEIVING BAG AND SET FOR SURGERY COMPRISING A TISSUE RECEIVING BAG

(71) Applicant: Tavigny B.V., The Hague (NL)

(72) Inventor: Jacqueline Therese Rose Rhemrev-Pieters, The Hague (NL)

(73) Assignee: Tavigny B.V., 's-Gravenhage (NL)

( * ) Notice: Subject to any disclaimer, the term of this patent is extended or adjusted under 35 U.S.C. 154(b) by 142 days.

This patent is subject to a terminal disclaimer.

(21) Appl. No.: 16/947,318

(22) Filed: Jul. 28, 2020

(65) Prior Publication Data

US 2020/0352599 A1    Nov. 12, 2020

Related U.S. Application Data

(63) Continuation of application No. 15/556,362, filed as application No. PCT/NL2016/050162 on Mar. 9, 2016, now Pat. No. 10,736,660.

(30) Foreign Application Priority Data

Mar. 9, 2015   (NL) .................................... 2014426

(51) Int. Cl.
*A61B 17/34* (2006.01)
*A61B 17/00* (2006.01)
(Continued)

(52) U.S. Cl.
CPC .... *A61B 17/3439* (2013.01); *A61B 17/00234* (2013.01); *A61B 17/3462* (2013.01); *A61B 90/40* (2016.02); *A61B 2017/00022* (2013.01); *A61B 2017/00026* (2013.01); *A61B 2017/00123* (2013.01); *A61B 2017/00287* (2013.01);
(Continued)

(58) Field of Classification Search
CPC .... A61B 17/00234; A61B 2017/00287; A61B 2017/00557; A61B 2017/320024; A61B 2017/3441; A61B 2017/3466
See application file for complete search history.

(56) References Cited

U.S. PATENT DOCUMENTS

| | | | |
|---|---|---|---|
| 6,537,273 B1 | 3/2003 | Sosiak | |
| 9,044,210 B1 | 6/2015 | Hoyte et al. | |

(Continued)

FOREIGN PATENT DOCUMENTS

| WO | WO 2014/207077 | 12/2014 | |
|---|---|---|---|
| WO | WO-2015084769 A1 * | 6/2015 | ....... A61B 17/00234 |

OTHER PUBLICATIONS

International Search Report from PCT/NL2016/050162 dated Jul. 20, 2016.

*Primary Examiner* — Christine H Matthews
(74) *Attorney, Agent, or Firm* — Quarles & Brady LLP (57) ABSTRACT

The invention relates to a tissue receiving bag for use in surgery, especially laparoscopic surgery, wherein the bag comprises at least one tissue receiving opening for receiving tissue and/or an instrument opening, especially a morcellator opening, wherein the bag comprises at least one further opening into the bag, wherein a flexible tube extends from said further opening having a free end comprising an insertion opening for inserting an instrument into the bag, wherein the bag preferably is inflatable.

21 Claims, 5 Drawing Sheets

(51) Int. Cl.
*A61B 90/40* (2016.01)
*A61B 17/32* (2006.01)

(52) U.S. Cl.
CPC ........... *A61B 2017/00557* (2013.01); *A61B 2017/320024* (2013.01); *A61B 2017/3435* (2013.01); *A61B 2017/3441* (2013.01); *A61B 2017/3466* (2013.01)

(56) References Cited

U.S. PATENT DOCUMENTS

| | | |
|---|---|---|
| 9,877,739 B2 | 1/2018 | Hoyte et al. |
| 10,555,747 B2 | 2/2020 | Hoyte et al. |
| 10,736,660 B2 * | 8/2020 | Rhemrev-Pieters ......................... A61B 17/3439 |
| 2005/0059865 A1 | 3/2005 | Kahle |
| 2014/0236167 A1 | 8/2014 | Shibley |
| 2015/0305728 A1 | 10/2015 | Taylor |
| 2016/0104394 A1 | 4/2016 | Miyazaki |

* cited by examiner

TISSUE RECEIVING BAG AND SET FOR SURGERY COMPRISING A TISSUE RECEIVING BAG

RELATED APPLICATIONS

This application is a continuation application of U.S. application Ser. No. 15/556,362, filed Sep. 7, 2017, which is a 35 U.S.C. § 371 national phase application of PCT/NL2016/050162 (WO 2016/144170) filed on Mar. 9, 2016, each entitled "Tissue Receiving Bag and Set for Surgery Comprising a Tissue Receiving Bag", which application claims the benefit of Netherlands Application No. 2014426, filed Mar. 9, 2015, each of which is incorporated herein by reference in its entirety.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

TECHNICAL FIELD

The invention relates to a tissue-receiving bag for use in surgery, especially laparoscopic surgery. The invention further relates to a set for surgery, especially laparoscopic surgery, comprising a tissue-receiving bag.

BACKGROUND

During surgery for removing tissue from a human or animal body, use can be made of a tissue-receiving bag for containing the tissue before and during removal of the tissue. An instrument can be used for morcellation of the tissue within the tissue receiving bag, in order to be able to easily remove the tissue even through a relatively small opening, such as for example during endoscopic surgery. Such instrument can be referred to as a morcellator.

WO2013/093030 discloses a tissue-receiving bag, which is referred to as a pneumoperitoneum device, for containing and morcellating tissue inside a cavity in a human body. In this device a collar is placed in an incision, through which collar the bag is introduced into the cavity. Tissue is cut from the body in the cavity using instruments inserted through said collar, for example inserted through a multi port closure placed on said collar, which tissue is then introduced in the bag through an opening. Then the opening is pulled out through the incision and, after removal of the closure, mounted on the collar, after which the closure is placed back, locking the neck of the bag 1 in place. Then, the tissue inside the bag can be treated by instruments inserted through the closure. The bag can be inflated inside the cavity when the closure is in place.

WO2013/075103 discloses a tissue receiving bag, comprising a tissue receiving opening closable by a Zip Lock® type closure. Several instrument ports have been provided in a wall of the bag.

Since April 2014 the Food and Drug Administration (FDA) discouraged its use for uterine procedures, issuing a warning that morcellators may spread occult cancer in the course of fibroid removal. A second warning was followed in November of the same year. One of the major suppliers of morcellator subsequently suspended sale of its morcellators until the role of morcellation will have been clarified by the FDA and the medical community, and later pulled its morcellators from the market.

In the same statement the FDA released a statement discouraging the use of power morcellators in patients seeking hysterectomy (removal of uterus through lower abdomen) and myomectomy (surgery to remove uterine fibroids—also called leiomyomas) procedures. The FDA suspects that nearly 1 in 350 patients, that are undergoing these procedures with the power morcellators, are at risk for having unsuspected uterine sarcoma, which can have major life altering consequences that the patient should not have to suffer for.

Morcellation is associated with spreading of cellular material of the morcellated tissue. In gynecologic surgery for benign pathologies there has been reported that there is approximately a 0.09% risk of an unexpected leiomyosarcoma. After morcellation 64% of such cases may develop disseminated disease which is of particular concern because of the considerable mortality of leiomyosarcoma. Morcellation of the more frequent benign leiomyoma variants may also cause disseminated disease, which while not associated with increased mortality is frequently inoperable and therefore much more difficult to manage than the original disease.

Thus there is a need for equipment suitable for surgery for removal of tissue from a human or animal body, using a tissue receiving bag in which the tissue can be safely morcellated and contained inside the bag, before and during removal of the morcellated tissue from the body. Such equipment may include an improved morcellator.

There is furthermore a need for a tissue-receiving bag for use in surgery including morcellating tissue inside the body, especially inside the bag, containing the morcellated tissue. Preferably such a tissue-receiving bag is sufficiently safe to aid in overcoming the objections raised by the FDA.

Furthermore there is a need for improved surgery including a morcellator step of tissue to be removed from a human or animal body.

Some of these needs can be fulfilled at least in part by products, systems and methods according to this disclosure.

The present invention is directed toward overcoming one or more of the problems discussed above.

SUMMARY OF THE EMBODIMENTS

In an aspect a tissue-receiving bag for use in surgery, especially laparoscopic surgery, according to this disclosure can be inflatable and comprises at least one tissue receiving opening for receiving tissue, and an instrument opening. The tissue-receiving opening can be the same as the instrument opening or they can be separate openings, spaced apart from each other. At least one instrument opening can be a morcellator opening. The bag comprises at least one further opening into the bag, wherein a flexible tube extends from said further opening. The said tube has a free end comprising an insertion opening for inserting an instrument into the bag.

With an operating bag according to the disclosure a morcellator can be inserted into the bag through the morcellator opening whereas the further instruments can be inserted into the bag through the at least one further opening. The further instrument can be inserted through the flexible tube, for example when the free end thereof has been pulled out of the body in which the bag has been inserted. Preferably the instrument opening and the at least one further opening are positioned on the bag some distance apart. The tube preferably has a length, at least in an extended position, such that the free end thereof can be pulled out through a laparoscopic incision in the body spaced apart from an opening through which the morcellator instrument can be inserted into the bag.

Preferably the tube is arranged such that the further instrument can be inserted into and pulled out of the tube and hence of the bag from outside the body. Preferably the instrument can at least be pulled out of the tube and hence out of the bag without touching the body, such that the risk of transfer of tissue, such as body cells, from the instrument to the body.

Preferably the free end of the tube can be closed outside the body when extending out of the body through an incision, before being retracted into the body through said incision. Thus the risk of tissue, such as body cells leaving the bag through the said opening is mitigated and contamination is prevented substantially.

A bag according to this disclosure can have multiple such openings to which a tube is or can be connected, especially a flexible tube. Each tube can be an integral part of the bag.

A tissue bag according to the present disclosure preferably is suitable for at least introduction into a human or animal body through a first opening in the body, especially a first incision, introducing tissue into the bag through a tissue opening, closing the tissue opening, pulling a free end of the at least one tube out of the body through a second incision, especially a second laparoscopic incision, introducing a morcellator into the bag through the instrument opening and introducing a further instrument into the bag through the free end of the tube. Preferably the bag is suitable for containing morcellated tissue inside the bag, closure of the free end of the at least one tube outside the body, retracting at least one tube into the body through the second incision and retracting the bag from the body through the first opening.

In this way a tissue-receiving bag can be provided with a tissue receiving opening and an instrument opening, especially a morcellator insertion opening, spaced apart from the tissue receiving opening. The tissue receiving opening can be provided with closing means such as a zipper, Ziploc® type closure, adhesive, Velcro® type closure or the like, for closing the tissue receiving opening, especially inside a body cavity after receiving tissue inside the bag through said tissue receiving opening. The tissue receiving opening when fully open may be larger that the instrument opening. The instrument opening may be provided by a flexible tube or neck of the bag having a cross section smaller than that of the tissue receiving opening, when fully open. The bag can be designed such that during use the instrument opening can be held outside a body cavity, whereas the rest of the bag has been inserted into said cavity through an incision in the body, wherein the tissue receiving opening can be opened and closed inside said body and instruments can be inserted into and through the bag, extending through the instrument opening and the tissue receiving opening when open.

An operating set according to this disclosure can comprise a bag which comprises at least one tissue receiving opening for receiving tissue, and an instrument opening, especially a morcellator opening. The bag may comprise at least one further opening into itself, wherein a flexible tube extends from said further opening. The tube has a free end comprising an insertion opening for inserting an instrument into the bag. The set further comprises at least a morcellator instrument. The bag and/or the instrument comprise at least one indicator for preventing the morcellator puncturing the bag. The set preferably is especially suitable for laparoscopic surgery.

The operating set may further comprise at least one further instrument, insertable through a tube and further opening of the bag, wherein the further opening and/or the tube can be sealingly closed around said further instrument when extending through said tube and/or further opening. The further instrument preferably is one of an endoscope, a camera, a catheter, a cannula, tongs or scissors.

In an aspect a method disclosed for morcellating surgery comprises using a tissue-receiving bag which comprises at least one tissue receiving opening, and an instrument opening, especially a morcellator opening, wherein the bag comprises at least one further opening into the bag, wherein a flexible tube extends from said further opening having a free end. This method may comprise at least the steps of introduction of the tissue receiving bag into a human or animal body, through a first opening in the body, especially a first incision, introducing tissue into the bag through the tissue opening, closing the tissue opening, pulling a free end of the at least one tube out of the body, preferably through a second incision, especially a second laparoscopic incision, introducing a morcellator into the bag through the instrument opening and introducing a further instrument into the bag through the free end of the tube.

The method may further comprise the steps of morcellating tissue inside the bag, containing the morcellated tissue inside the bag, closing the free end of the at least one tube outside the body, retracting the at least one tube into the body through the second incision and retracting the bag from the body through the first opening.

Various modifications and additions can be made to the embodiments discussed without departing from the scope of the invention. For example, while the embodiments described above refer to particular features, the scope of this invention also included embodiments having different combination of features and embodiments that do not include all of the above described features.

BRIEF DESCRIPTION OF THE DRAWINGS

In further elucidation of the present invention embodiments of the present disclosure, such as embodiments of a tissue-receiving bag, an operating set and an operating method shall be described hereafter, with reference to the drawings. In the description a tissue-receiving bag may also be referred to as a morcellator bag. Therein shows:

FIG. 3A-C schematically three steps of retracting an instrument from a tube of a tissue receiving bag;

DETAILED DESCRIPTION

In this description, embodiments of the invention will be described with reference to the drawings by way of example only. These embodiments should by no means be understood as limiting the scope of the disclosure. At least all combinations of elements and features of the embodiments shown are also considered to have been disclosed herein. In this description the same or similar elements and features will be referred to by the same or similar reference signs.

In this description expressions of orientation such as top, bottom, vertical et cetera are used for convenience only and refer to the orientation of the module as seen in the accompanying drawings. Such expressions are not to be regarded as limiting the orientation of the module in use, and indeed, as will be described below, bags and instruments such as morcellators according to the description can be used in other orientations.

A tissue receiving bag 1 according to the disclosure can be used for surgery, especially but not limited to laparoscopic or minimal invasive surgery, for removal of tissue from a human or animal body, such as for example but not limited to hysterectomy, removal of cancerous and/or benign tissue or cists, or of organs. Tissue may for example and not exclusively be all or part of the uterus, ovaries, fibroids, spleen, kidneys, intestine, or any dissected tissue to be removed safely from said body.

A tissue receiving bag according to this disclosure can preferably be closed during and after surgery such that at least all parts of the bag, including the or each tube, that pass into and/or through the body of a patient are firmly closed when tissue is treated inside the bag and retrieved from the body from the bag or with the bag, whereas the at least one additional tube provides access into the bag when so desired. No tissue matter can therefore escape into the body from the bag when the tissue receiving opening has been closed.

Figure 1:
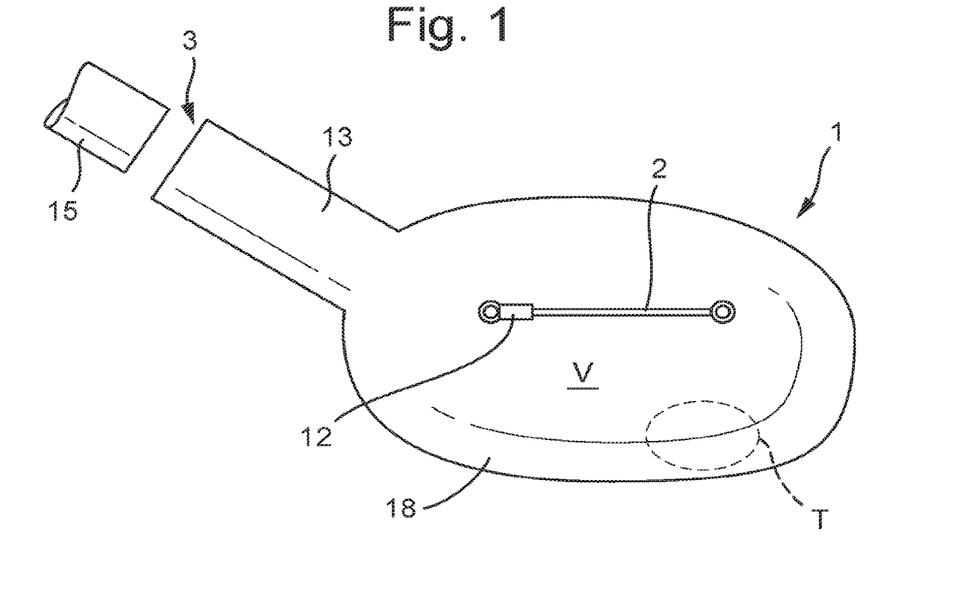
FIG. 1 schematically an embodiment of a tissue-receiving bag, in perspective view.

FIG. 1 shows schematically a tissue-receiving bag 1 for use in surgery, especially laparoscopic surgery. The bag 1 can be made of plastic, such as transparent plastic, or for example of rubber. The bag 1 is flexible, such that it can be collapsed to be inserted through an incision into an opening or cavity in a human or animal body B. The bag 1 may be inflatable, in a suitable manner, as will be explained. The bag 1 may comprise at least one tissue receiving opening 2 for receiving tissue T, for example tissue to be removed from the body B. The bag 1 may comprise at least one instrument opening 3, for introducing at least one instrument 15. The at least one-instrument opening 3 may be a morcellator opening 3.

Figure 2:
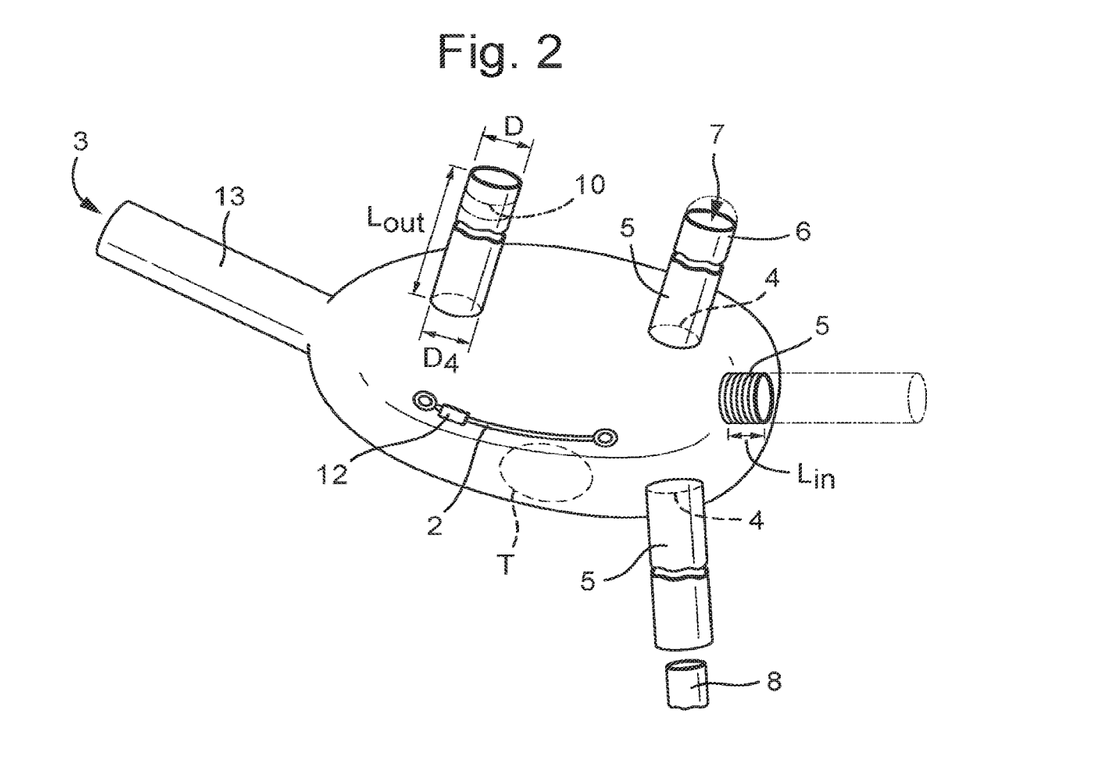
FIG. 2 schematically an embodiment of a tissue-receiving bag, in perspective view, having tubes provided at further instrument openings.

As shown in FIG. 2 the bag 1 can comprise at least one further opening 4 into the bag 1. A flexible tube 5 extends from said further opening 4 having a free end 6 comprising an insertion opening 7 for inserting an instrument 8 into the bag 1.

In this description a tube 5 should be understood as meaning at least a tubular element which is at least partly flexible and preferably made of plastic or rubber. A tube 5 can be an integral part of the bag 1 or can be connectable to the bag 1, for example using a known coupling element, or can be mounted to the bag 1, for example by sealing, welding, gluing or any other suitable means. A tube 5 can for example be pleated, such that in a first position, as for example shown in FIG. 1, it has a relatively short length Lin between the free end 6 and the opening 4, whereas in a second position, for pulled into an extended state, it has a far longer length Lout. A tube 5 may have an internal cross section D which is smaller than the length Lout when in said extended state. The cross section D may be relatively small compared to the size of the tissue receiving opening when fully opened. In a bag 1 having multiple tubes 5, the tubes may have all the same or different dimensions. In an extended state of the tube 5 the tube may have a length Lout between the further opening 4 and the free end 6 which is at least five times the diameter D4 of the further opening 4. The tube 5, at least in the extended state of the tube 5, has a length Lout suitable for during use bringing the free end 6 of the tube 5 outside a human or animal body B through a laparoscopic incision 9 when the bag 1 has been inserted into a body cavity C of the human or animal body B. A longitudinal direction of the tube 5 should be understood as meaning a direction between the opening 4 to which it is connected and the free end 6 thereof.

The free end 6 of the tube 5 may be provided with at least one closing element 10 for closing the free end 6 of the tube 5 and preferably for sealing the tube 5 around an instrument 8 when inserted into the tube 5 through the free end 6 or at least through the insertion opening 7. Such closing element 10 can for example be a tie rope or an elastic band. In embodiments the closing element 10 can comprise a gel port or the like self-closing element. Preferably the element 10 closes air tight around the instrument. In embodiments the end 6 can be provided with a seal 10 cooperating with a seal provided on the instrument 8, for example comparable to a Luer lock-type connection.

Figure 3A:
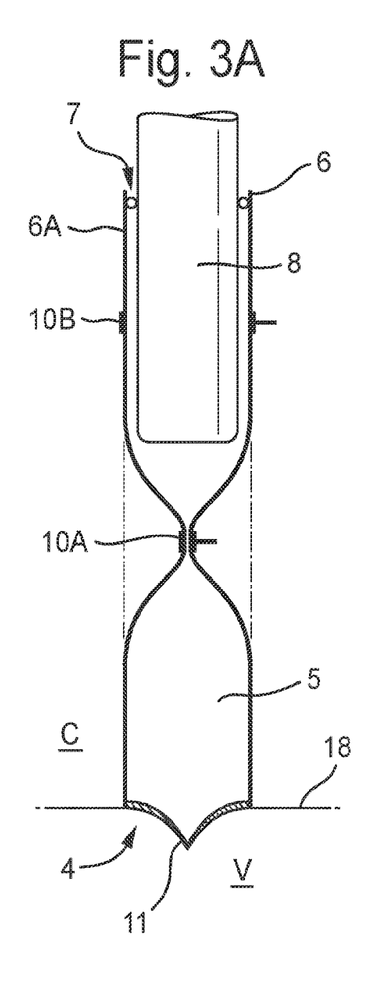

In embodiments the free end 6 of the tube 5 is closed, at least prior to use of the bag 1, by at least one of a tube portion, a closure or a valve. In an embodiment the free end 6 may be closed by part of the tube 5 itself, for example a seal of the tube such as shown in FIG. 3 by pressing the tube flat and sealing the wall thereof against itself. The closed end can for example be severed in order to provide access to the insertion opening 7, for example by cutting off the free end of the tube 5.

In embodiments the further opening 4 can comprise a closure 11. The closure 11 preferably is a self-closing closure or seal for sealing around an instrument 8 inserted through said further opening. Such closure 11 can for example be a gel port, as known in the art, or a duck bill type valve as shown in FIG. 3.

In embodiments the tube 5, especially at least the free end thereof can be designed such that after removal of the instrument 8 from the tube 5 the free end 6 can be closed again, in order to avoid gas and/or fluids and, especially, bodily tissue such as but not limited to body cells leaving the bag through said tube 8. In embodiments the closing 10 as discussed can be used for reclosing said end 6. The closing element 10 can for example be an elastic band or string that can be pulled tight around the instrument 8 and after removal of the instrument. In embodiments a closure element 10 can be a self-closing element, such as a duck bill type valve, which can be pushed open when inserting an instrument 8 but will be pushed closed, for example by gas inside the bag, when the instrument is not present in the tube 5.

FIG. 3 shows an embodiment of part of a tube 5 including a free end 6 thereof, which comprises at least two closures and/or seals 10A, 10B, spaced apart longitudinally, for closing the tube and/or sealing against an instrument extending through said tube.

During use after removal of an instrument 8 from the tube 5 first the free end 6 can be folded or pushed inward back into the tube 5 after which a closure 10, especially one of at least two closures 10, especially the second closure 10B can be closed or pulled tight, closing the tube 5 and securing the free end 6 inside the tube 5. Since the only part of the tube 5 that could be in contact with the instrument 8 and might thus be contaminated with for example body cells is the inside of the tube 5 and possibly the edge of the insertion opening 7 or a directly adjacent part of the free end 6, by confining this inside the tube itself, closed off from the environment, contamination of the environment is prevented.

Figure 3B:
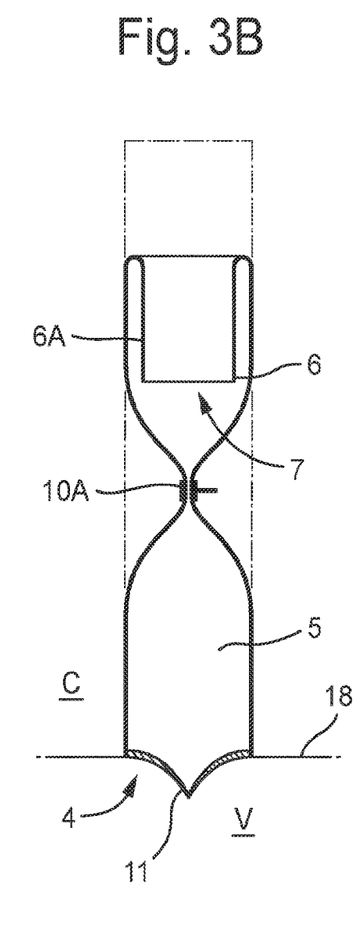
Figure 3C:
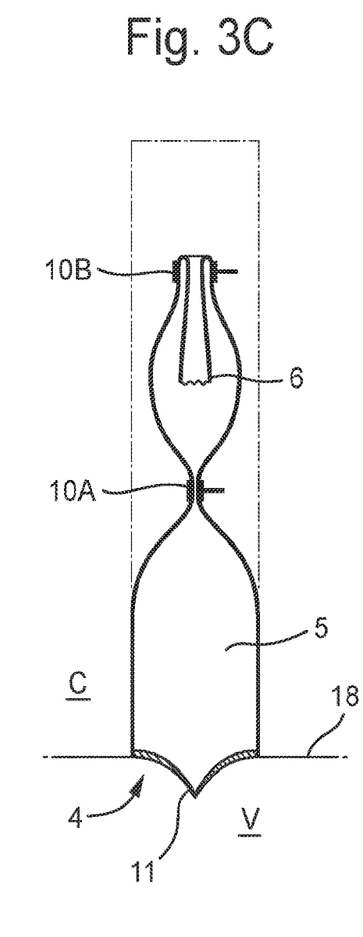

If two closures 10A, 10B are provided, one of the closures 10A, especially the closure closest to the opening 4 can be closed before the instrument 8 is fully retracted (FIG. 3A), preventing tissue from leaving the tube 5 and possibly preventing deflation of the bag 1. Then the other closure 10B can be closed in a manner as described here above, by first folding or pushing the free end 6 back into the tube 5 (FIG. 3B) an then closing the second closure 10B (FIG. 3C).

In embodiments the bag is provided with a series of further openings 4. A flexible tube 5 can extend from some or each further opening 4. In embodiments each further opening 4 can be spaced apart from the tissue receiving opening 2 and from the instrument opening 3. This will ease working on tissue within the bag 1 with different instruments, such as a morcellator and for example a camera, scissors, graspers or the like, from different angles.

The tissue receiving opening 2 is preferably provided with a closing mechanism 12 for closing the opening 2 after tissue T has been received inside the bag 1. Such closing mechanism can for example be a zipper, Ziploc® type closure, adhesive strips, Velcro® type locking or any such suitable means for closing the opening 2, preferably air and liquid tight. Alternatively or additionally the bag 1 can be foldable such that the opening 2 can be closed after receiving the tissue T.

In embodiments a further tube 13 can extend from or can define the instrument opening 3. Said further tube 13 and/or the instrument opening 3 can comprise a closure and/or seal 14 for closing and sealing the tube 13 around an instrument 15 extending through said tube and/or for closing the tube 13 when such instrument 15 has not been inserted into the opening 3 or is retracted from said instrument opening 3. The tube 13 will have a longitudinal length L13 making it easy to keep an end 16 of the tube 13 outside the body or at least outside an incision 9 through which the bag 1 is inserted, in order to provide easy access into the bag 3, easy connection to the bag 1, for example for instrumentation or for removal of the bag 1 from a cavity C. Moreover this may prevent contamination of the incision 9 when an instrument 3 is retracted or when the bag 1 is removed.

In embodiments a closure and/or seal 14 at the opening 3 of the bag 1 can be an integral part of the bag 1. In embodiments a closure and/or seal 14 at the opening 3 can be a multi port closure as conventionally used with tissue receiving bags 1 of the prior art. Such multi port closure is for example known from WO2013/093030. Such closures are well known in the art, such as for example but not limited to TriPort15 or SILS ports.

In preferred embodiments a tissue receiving bag 1 according to the disclosure is suitable for at least introduction into a human or animal body B through a first opening in the body, especially a first incision 9, introducing tissue T into the bag through the tissue opening 2 and closing the tissue opening 2. A free end 6 of at least one tube 5 can then be pulled out of the body B, preferably through a second incision 17, especially a second laparoscopic incision 17. The free end can thereby be brought outside the cavity C and preferably also outside the body B. During surgery then at least part of an instrument such as for example a morcellator 15 can be introduced into the bag 1 through the instrument opening 3, whereas a further instrument 8 can be introduced at least in part into the bag 1 through the tube 5, by inserting it through the opening 7 of the tube 5. If several such tubes 5 are provided several entries into the bag can be created in this way.

Preferably the bag 1 is further suitable for morcellation of and/or otherwise treating the tissue T inside the bag and containing morcellated tissue T inside the bag 1. Preferably the free end 6 of the at least one tube 5 outside the body B can be closed during and/or after retraction of the relevant further instrument 8 from said tube 5, preferably gas and liquid tight. Then the at least one tube 5 can be retracted into the body through the relevant second incision 17, back into the cavity C in which the bag 1 is situated. The bag 1 can be retracted from said cavity C and the body B through the first opening or incision 9. Since the free end 6 of the tube 5 has been closed prior to retraction into the cavity, contamination of the cavity C by any tissue related matter, such as cells is prevented, since this matter cannot leave the bag 1.

Alternatively the instrument opening 3 can be closed and the bag be retracted through the same or a second incision 17 or further incision or natural or man made body opening.

It is preferred that the instrument 8 is retracted into the tube 5 in part, such that it can be closed between an end 8' of the instrument closest to the main volume V of the bag 1 and said main volume V, before retracting the instrument fully from the tube, preventing matter, such as tissue cells being forced out of the bag before closing the tube 5. Then, when the instrument 8 has been retracted fully, preferably the free end 6 of the tube 5 is inserted into the tube 5, for example pushed or folded back, where after the tube 5 is again closed at the then free end 6A thereof, containing the original free end 6 within the tube 5, between the two closures. Thus contamination of the body B with matter from the bag is even better prevented, especially during retraction thereof into the cavity and when being pulled out through the first opening or incision 9. For such method especially but not exclusively a bag 1 as for example shown in FIG. 2 would be suitable.

In embodiments the bag 1 can be inflatable. In embodiments the bag 1 can be inflatable by inserting gas such as air into the internal volume V of the bag 1, for example through one of the openings 2, 3, 7. Obviously such bag 1 then preferably is air tight, including closures of all relevant openings. By inflating the bag 3 the internal volume V of the bag 1 can be kept open, which at least facilitates working inside the bag 1 by creating a substantially unobstructed working area. Moreover this reduces the risk of the instruments 8, 15 damaging the bag 1, especially puncturing the wall 18 of the bag 1 since the bag 1 will be expanded.

Figure 4:
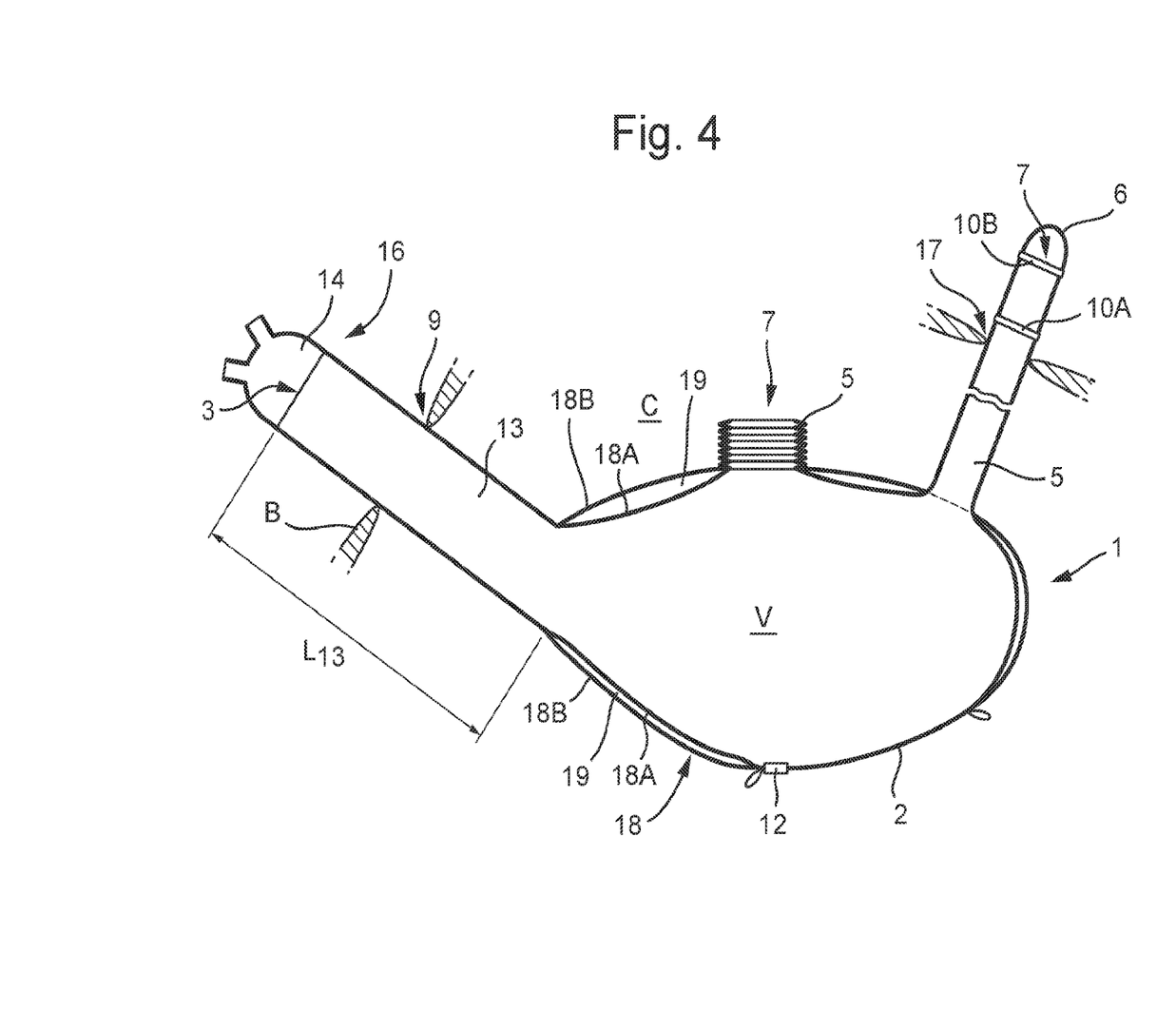
FIG. 4 schematically in cross section part of a tissue receiving bag, with a tissue receiving opening and a further instrument opening.

In embodiments, as for example shown in FIG. 4, a tissue-receiving bag 1 can have a multi layered wall part 18. In embodiments a gas and/or fluid can be provided between at least two of the layers 18A, 18B of said wall part 18. In embodiments the gas or fluid inserted in between the layers 18A, 18B can be used for inflating the bag 1. In such embodiment the internal volume V may be kept at substantially atmospheric pressure or at least does not to be pressurized. Alternatively or additionally the at least two layers 18A, 18B can be used for enforcing the bag 1. In embodiments the space 19 between two layers 18A, 18B can be used for detecting a leak in one of the two layers 18A, 18B, for example by measuring the pressure of the gas or fluid in said space 19. When said pressure drops the integrity of at least one of said layers 18A, B may have been compromised, for example by puncturing the inner wall 18A by an instrument, such as the morcellator. Alternatively the bag can be observed, for example using a camera, for fluid flowing into the inner volume V and/or into the cavity C from the space

19. To which end preferably the fluid or gas is colored or at least made detectable by the camera or a sensor supplied for the same, such that fluid or gas escaping from the space 19 can easily be detected.

According to the invention an operating set, especially for laparoscopic surgery can comprise a bag according to any one of the previous claims and at least one morcellator instrument, wherein the bag and/or the instrument comprise at least one indicator for preventing the morcellator puncturing the bag.

In embodiments of a tissue receiving bag, such as a bag 1 as disclosed in this description or as known in the art, at least part 18C of a wall 18 of the bag 1 is electrically conductive. An instrument 8, 15, such as a morcellator, to be used inside the bag 1 can then be provided with at least one appropriate contact 20, such that when said contact 20 is brought into contact with the electrically conductive wall part 18 an electric circuit is closed and an alarm 25 given, for example audible and/or visible, and/or the instrument is shut off. This can for example be indicative for a situation in which a part of the instrument 8, 15 is too close to said wall, risking puncture or otherwise damage of the bag 1. Alternatively or additionally said sensor can be or comprise a contact or pressure sensor. Alternatively or additionally the wall 18 of the bag 1 can for example be at least partly reflective for electromagnetic waves, such as but not limited to light or sound, e.g. ultra sound, transmitted from a transmitter 21 provided on the instrument 8, 15, wherein a sensor 22 is provided for receiving waves reflected from said reflective wall part 18. Based on the waves detected by said sensor 22 then the distance of a relevant part of the instrument 8, 15, for example the distance between the wall 18 of the bag 1 and a morcellator head 15A can be deduced, which can again be indicative for a situation in which a part of the instrument 8, 15 is too close to said wall, risking puncture or otherwise damage of the bag 1. This can be used for example for giving an alarm 25 and/or for shutting off the instrument 8, 15.

In more general terms an operating set 23 of a tissue receiving bag 1 for example but not limited to a bag 1 according to this disclosure and an instrument 8, 15 can be designed such that at least one of the bag 1 and/or the instrument 8, 15 comprise at least one indicating system 18, 20, 21, 22 for preventing the instrument 8, 15, especially a morcellator puncturing the bag 1. This may prevent the risk of tissue and/or body fluids, such as morcellated tissue, cells or the like to leak from the bag 1 back into the body, which could result in infection or spreading cells which may be cancerous or otherwise detrimental to the patient's health.

In these embodiments the indicating system 18, 20, 21, 22 can be designed to measure or otherwise detect a distance between a cutting or puncturing end of the relevant instrument and a wall part 18 of the bag 1 close thereto, such that if said distance is reduced below a predefined limit an alarm is given and/or the instrument 8, 15 is shut off or is otherwise prevented from damaging said wall of said bag. The said limit may be zero, meaning that said alarm is given or said instrument is shut off or brought into an idling state when a relevant part of the instrument contacts the wall of the bag. For example as long as said instrument contacts said bag.

An operating set 23 according to this disclosure can comprise a tissue-receiving bag 1 and at least one instrument, especially a morcellator 15. Such an operating set can further comprise at least one further instrument 8 insertable through a tube 5 and a further opening 4 of the bag 1. The further opening 4 and/or the tube 5 can preferably be sealingly closed around said further instrument 8 when extending through said tube 5 and/or further opening 4. Such further instruments can for example be one of but not limited to an endoscope, a camera, a catheter, a cannula, grasper or scissors. An example of a morcellator can be a Storz morcellator.

With an operating set 23 according to the disclosure surgery can be performed, for example as follows.

After proper preparation of a patient 30 a first incision 9 is made in the body B, opening into a body cavity C. The tissue-receiving bag 1 is folded and then introduced into the cavity C through the first incision 9. The instrument opening 3 is held outside the cavity C, a part of the bag 1, for example a further tube 13 forming a neck portion of the bag 1 extending through the incision 9. Tissue T to be removed, for example and not limited to all or part of the uterus, ovaries, fibroids, spleen, kidneys, intestine, or any dissected tissue to be removed safely from said body, is cut from the body B inside the cavity, for example by introducing a dissecting instrument 8A into the body cavity C through a second incision 17, in a known manner. The tissue T preferably is held by an appropriate instrument 8B, such as graspers, during dissection, in order to manipulate the tissue during dissection and to prevent the tissue T from dropping in the cavity C. In embodiments the instrument 8B can be inserted into the body cavity C through a third incision, but preferably the said instrument 8B is inserted through the instrument opening 3 or through a further opening 4, extending through the bag 1 and out of the tissue receiving opening 2, such that after dissection the tissue can be retracted into the bag 1 through the tissue receiving opening 2 without for example having to transfer it to a further instrument. In embodiments the bag could be moved over the tissue to be dissected prior to dissection, by moving the tissue-receiving opening over the tissue T and dissecting the tissue T inside the bag. In such embodiment the dissecting instrument 8A could also be inserted into the bag through the instrument opening 3, or through a further opening 4, preferably in a manner as will be described hereafter.

After having received the tissue T inside the bag 1, the tissue receiving opening 2 is closed, for example by the closing mechanism 12. Preferably the closure can be manipulated from the inner volume V of the bag 1. Alternatively the closure can be manipulated at least partly from the outside of the bag 1, for example by introducing an appropriate instrument such as graspers through a further incision.

On the instrument opening 3 preferably a closure 14 is provided, such as for example a multi port closure as indicated before, closing and sealing the opening 3. The bag 1 preferably is inflated by introducing a gas such as air into the interior volume V and/or, if a multi-layered wall is used, between two such layers 18A, B, as described. This will provide a large inner volume V of the bag 1 allowing the surgeon(s) sufficient space to manipulate the tissue T inside the bag without being obstructed by the wall 18 of the bag 1. The wall 18 of the bag 1 may push outward the wall of the cavity C.

The dissecting instrument 8A will be retracted from the second incision 17. An appropriate instrument, such as for example, graspers, will be inserted through a second incision 17, with which instrument an end 6 of a tube 5 will be grasped such that it can be pulled out through the second incision 17, such that the tube 5 passes the incision and free end 6 extends outside said body B or at least outside the cavity C. If the end 6 and/or the opening 4 from which the tube extends is closed no gas or tissue can leave the bag through said tube 5. Such closure can for example be obtained by one of the closures 10 or by an appropriate closure at the opening 4, for example but not limited to a gel port or a duck bill type valve, as known from the art and for example described in WO2013/075103.

The free end 6 outside the body B may be severed, for example be cut off, providing an opening 7 into the tube 5. Then an instrument 8, such as for example but not limited to graspers, scissors, endoscope, light source, suction device, flushing device, cannula, catheter or the like can be inserted into and through the tube into the inner volume of the bag 1. The instrument 8 will be shielded relative to the cavity C by the tube 5 and the bag 1. Preferably the tube 5 seals against an outside of the instrument 8 or appropriate seals are provided, for example a single or multi port closure 14A provided by or mounted on the opening 7 or in the opening 4, preventing gas and/or tissue such as cells or fluids to pass along the instrument 8.

Obviously more than one such tube 5 can be pulled through one or more incisions 9, 17, in a similar way, in order to provide different points of access into the bag 1 for instruments to be used during surgery. Each incision 9, 17 is preferably a laparoscopic, minimal invasive incision.

After closure of the bag 1, especially the tissue receiving opening 2, and preferably after inflating the bag 1, a morcellator 15 can be inserted into the inner volume V of the bag 1, in order to morcellate the tissue T inside the bag. Such morcellators (both electromechanical and bipolar cutting) are well known in the art and shall not be discussed here in any detail. In embodiments during morcellation of the tissue the morcellated tissue can be retrieved from the bag 1, for example by suction and/or extraction with graspers through the morcellator itself and/or through a suction instrument inserted into the bag through a tube and further opening 4. Alternatively, the tissue, before, during and after morcellation can be contained by the bag 1, inside the inner volume thereof, to be removed from the cavity together with the bag 1.

Figure 5:
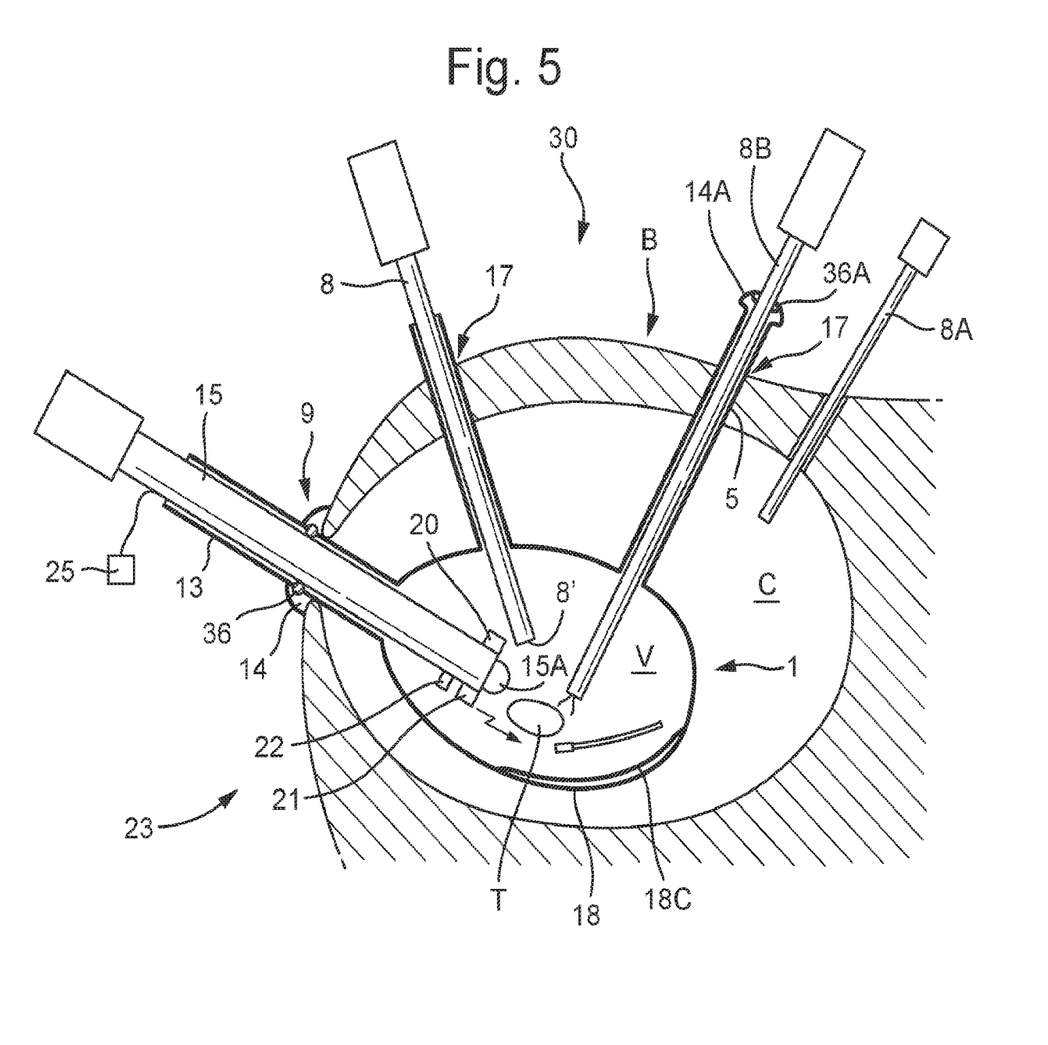
FIG. 5 schematically an instrument, for example a morcellator inserted into a tissue receiving bag according to the disclosure, provided with means for monitoring the position of an end of the instrument relative to the wall of the bag.

FIG. 5 shows the bag 1 inside the cavity C, tissue T contained inside the bag 1 and a morcellator 15 and further instruments 8 inserted through the tube 13 and the tube 5 respectively.

When an instrument 8 is no longer necessary for use in the bag 1 it may be retracted from the relevant tube 5. Preferably, to this end firstly the instrument 8 is retracted following the procedure as described with reference to FIG. 3. The instrument is first retracted partly, such that the end 8' is situated between the opening 4 and the opening 7 and, preferably, between the first and second closures 10A, 10B, preferably in a part of the tube extending outside the relevant incision 9, 17 in body B. Then the internal passage of the tube 5 between the end 8' and the opening 4 is closed off, for example by the first closure 10A. Thus gas and, especially tissue matter such as cells cannot pass said closure 10A. Then the instrument may be retracted from the tube completely. The free end 6 of the tube 5 can then be pushed back into the inner passage of the tube 5, such that any tissue matter that might be transferred from the instrument onto an edge portion 6A of the tube is contained within the inner passage of the tube 5. Then the second closure 10B is closed, locking said edge portion 6A within the tube 5.

When the bag 1 is to be retrieved from the cavity C any tube 5 used will be closed as discussed. Then the bag 1 can be retrieved by pulling it out of the cavity C through one of the incisions 9, 17. Preferably the bag 1 is retrieved through the largest incision or the least conspicuous incision. The bag may also be inserted and/or retrieved per vaginam, through the Fossa Douglasi or through any orifice appropriate for the performance of the surgical techniques, for example techniques now known as Natural Orifice Translumenal Endoscpopic Surgery (NOTES®) surgery. The bag can for example be retrieved through the first incision 9. In such embodiment the or each tube 5 extending through another incision 17 will be pulled back into the cavity C before being pulled out of the cavity C with the bag 1. Since the free ends 6 have been properly closed, the possibly contaminated portions 6A thereof being well shielded, the risk of contamination of the cavity C is substantially eliminated.

In the embodiments of the method described the instrument opening 3 is kept outside the cavity C during the entire procedure. However it is also possible to first insert the entire bag 1 into the cavity C, dissect the tissue and position it into the bag 1 and then pull the instrument opening 3 back out through the first incision 9. This is especially suitable of the instrument opening 3 is also the tissue receiving opening 2, as is known in the art as for example described in WO2013/075103 and WO2013/093930. In such embodiments again one or more tubes connected to one or more further openings 4 may be pulled through further incision(s) as described here above, before, during and/or after bringing the instrument opening 3 back out through the first incision 9.

In embodiments for at least one and preferably all of the tubes 5 and/or for the tube 13 a cytotoxic valve or seal, such as for example but not limited to a gel port 36, 36A can be provided, preferably at a position outside the body B during surgery. Such cytotoxic provision can for example be incorporated into or be provided by the ports 14 and/or 14A or as separate provisions. In FIG. 5A these provisions 36, 36A are schematically shown as incorporated in the ports 14, 14A. During use and especially during retraction of an instrument 8, 15 from the respective tube 5, 13 a cytotoxic compound can be transferred to the instrument, for example through contact between the instrument and the cytotoxic provision, such that cells attaching to the instrument will be influenced by said compound. The cell viability will deteriorate by said compound in a known manner. Examples of such compounds can for example be but are not limited to fluids or gels formed by or containing for example one or more of the group of alcohol, iodine, betadine or any such known disinfecting or cytotoxic compound.

Preferably the cytotoxic provisions are mounted to or connected to or over the free end of the relevant tube 8, 13 outside the body, such that they can be removed from the relevant tube 5, 13 prior to the procedure as described, for example referring to FIG. 3 A-C, for retrieval of the bag 1 from the body B. Thus it is prevented that the cytotoxic compound is brought into the body B.

Figure 6A:
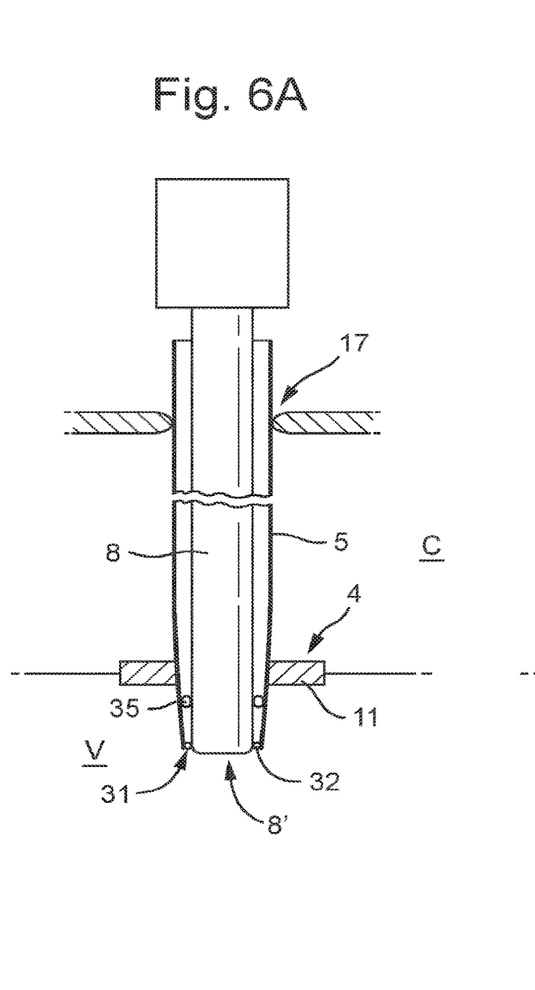
FIGS. 6A and B an instrument with a tube provided along a shaft thereof.
Figure 6B:
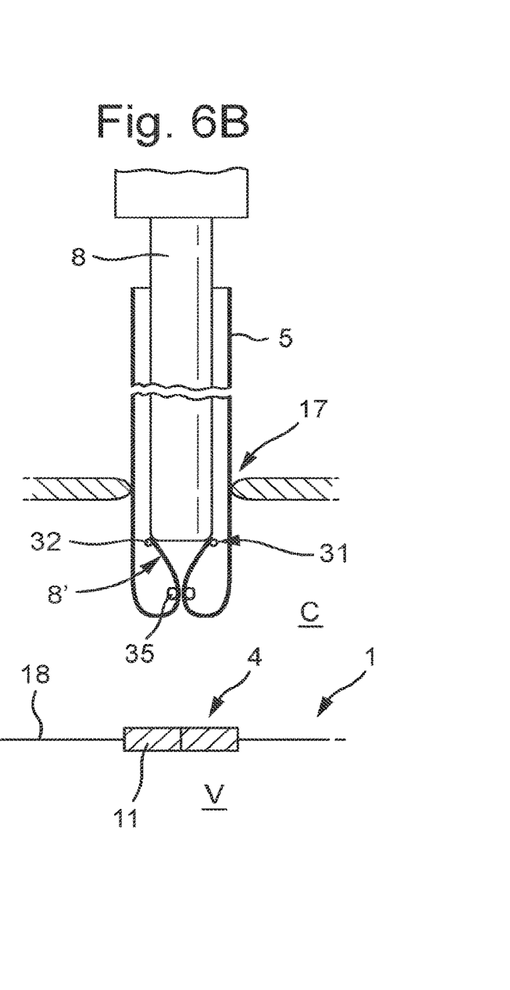

As discussed one or each tube 5 may be a part separate from the bag 1 and may be connectable to the bag 1, especially to a further opening 4 permanently or temporarily. In embodiments the tube can be provided with an instrument 8 to be introduced into the bag. As shown in FIG. 6 a tube 5 can be positioned over a shaft of an instrument 8. Preferably an end 31 of the tube 5 is connected to the instrument 8, preferably at or near the tip 8' thereof. When the instrument 8 is inserted through a second incision 17, the tube 5 is taken along with it and is inserted into the relevant further opening 4, for example a gel port or such self-closing opening or valve. In an embodiment the end 31 of the tube 5 can be provided with a connecting element 32, for example a clamping ring, click ring or dedicated connector for connecting the end 31 to the further opening 4 such that when the instrument 8 is retracted again said end 31 stays connected to said further opening 4. Alternatively the connector 32 can be such that when the instrument 8 is retracted from the opening 4 the end 31 of the tube 5 stays connected to the instrument 8, especially adjacent the tip 8' thereof, such that the end 31 of the tube is pulled into the internal passage of the tube 5 when retracting the instrument 8. Preferably the tube 5 is thereby made self-closing at least near the end 31, such that the internal passage is closed off after retraction of the tip 8', or an element 35 such as for example an elastic band such as an O-ring is provided near the tip 8', as shown in FIG. 6, which will be pulled off the tip 8' closing the passage of the tube 5 when pulling the instrument tip 8' back through the opening 4, which in this embodiment should be self closing. An advantage of such embodiments may be that a tube 5 only has to be provided for an opening when it is to be used.

The disclosure is by no means limited to the embodiments specifically described and shown in the drawings. Many variations therefor are possible and are also considered disclosed herein, including but not limited to all combinations and permutations of parts of the embodiments as shown and described, which are all considered having been disclosed herein. The bag 1 may be made of any suitable material or combinations of materials. In a bag having a multiple layered wall an inner wall may be more rigid that an outer wall, in order to obtain expansion substantially outward if inflated between the layers. Multiple tissue receiving openings could be provided. A bag 1 could have different compartments, some or all of which may be inflatable, whereas different tissue may be receivable in such compartments.

What is claimed is:

1. A tissue receiving bag for use in surgery, wherein the bag comprises at least one tissue receiving opening for receiving tissue, wherein the bag comprises at least one further opening into the bag, spaced apart from the at least one tissue receiving opening, wherein the at least one tissue receiving opening, when fully open, is larger than the at least one further opening, wherein a flexible tube extends from said at least one further opening, said flexible tube having a free end comprising an insertion opening for inserting an instrument into the bag, and wherein the free end, prior to insertion into a human or animal body, comprises at least one closing element for closing the free end of the tube.

2. The tissue receiving bag according to claim 1, wherein said at least one closing element is configured for sealing the tube around an instrument inserted into the tube through the free end.

3. The tissue receiving bag according to claim 1, wherein in an extended state of the tube, the tube has a length suitable for during use bringing the free end of the tube outside a human or animal body through a laparoscopic incision when the bag has been inserted into a body cavity of the human or animal body.

4. The tissue receiving bag according to claim 1, wherein the bag is inflatable.

5. The tissue receiving bag according to claim 1, wherein the at least one closing element is at least one of a tube portion, a closure or a valve.

6. The tissue receiving bag according to claim 1, wherein the flexible tube comprises at least one other closing element, longitudinally spaced apart, for closing the flexible tube or sealing against an instrument extending through said flexible tube.

7. The tissue receiving bag according to claim 1, wherein a further flexible tube extends from or defines at least one instrument opening into the bag, said further flexible tube comprising a closure or seal at or near a free end of said further flexible tube for closing or sealing the further flexible tube around an instrument extending through said further flexible tube or for closing the further flexible tube when said instrument is retracted from said at least one instrument opening.

8. The tissue receiving bag according to claim 1, wherein the at least one further opening forms an instrument opening, the instrument opening being spaced apart from the at least one tissue receiving opening.

9. The tissue receiving bag according to claim 1, wherein the bag is suitable for at least one of:
introduction into a human or animal body through a first opening in the body;
introducing tissue into the bag through the at least one tissue receiving opening;
pulling the free end of the flexible tube out of the body through a second opening in the body;
introducing a morcellator into the bag through the flexible tube; or
introducing a further instrument into the bag through the free end of the flexible tube.

10. The tissue receiving bag according to claim 9, wherein the bag is further suitable for at least one of:
containing morcellated tissue inside the bag;
closure of the free end of the flexible tube outside the body;
retracting the flexible tube into the body through the second opening; and
retracting the bag from the body through the first opening.

11. The tissue receiving bag according to claim 1, wherein the flexible tube extends from said at least one further opening in a direction away from an interior of the bag.

12. A tissue receiving bag for use in surgery, wherein the bag comprises at least one tissue receiving opening for receiving tissue, wherein the bag comprises at least one further opening into the bag, spaced apart from the at least one tissue receiving opening, wherein a flexible tube extends from said at least one further opening, said flexible tube having a free end comprising an insertion opening for inserting an instrument into the bag, wherein the free end, prior to insertion into a human or animal body, comprises at least one closing element for closing the free end of the tube, wherein the at least one further opening is one of a series of further openings, and wherein a further flexible tube extends from each of the series of further openings, each of said further flexible tubes being provided with at least one of said at least one closing element.

13. A tissue receiving bag for use in surgery, wherein the bag comprises at least one tissue receiving opening for receiving tissue, wherein the bag comprises at least one further opening into the bag, said at least one further opening being provided spaced apart from the at least one tissue receiving opening, wherein the at least one tissue receiving opening, when fully open, is larger than the at least one further opening, wherein a flexible tube extends from said at least one further opening, said flexible tube having a free end comprising an insertion opening for inserting an instrument into the bag, and wherein prior to insertion into a human or an animal body, the free end is closed by at least one of a tube portion, a closure or a valve operatively associated with the free end.

14. The tissue receiving bag according to claim 13, wherein the bag is inflatable.

15. The tissue receiving bag according to claim 13, wherein the tube has been formed prior to insertion of the bag into the human or the animal body.

16. The tissue receiving bag according to claim 13, wherein at least one further tube extends from or defines an instrument opening into the bag, each said at least one further tube comprising a closure or seal at or near a free end of said further tube for closing or sealing the tube around an instrument extending through said at least one further tube or for closing said at least one further tube when said instrument is retracted from said instrument opening.

17. The tissue receiving bag according to claim 13, wherein the flexible tube extends from said at least one further opening in a direction away from an interior of the bag.

18. A tissue receiving bag for use in surgery, wherein the bag comprises at least one tissue receiving opening for receiving tissue, wherein the bag comprises at least one further opening into the bag, said at least one further opening being spaced apart from the at least one tissue receiving opening, wherein a flexible tube extends from a periphery of said at least one further opening, said flexible tube having a free end comprising an insertion opening for inserting an instrument into the bag, wherein prior to insertion into a human or an animal body, the free end is closed by at least one of a tube portion, a closure or a valve, operatively associated with the free end, and wherein the flexible tube, prior to insertion of the bag into the human or the animal body, extends from a wall of the bag through said at least one further opening to said at least one tube portion, closure or valve.

19. A tissue receiving bag for use in surgery, wherein the bag comprises at least one tissue receiving opening for receiving tissue,
- wherein the bag comprises at least one further opening into the bag, wherein a flexible tube extends from said at least one further opening, said flexible tube having a free end comprising an insertion opening for inserting an instrument into the bag,
- wherein the at least one tissue receiving opening, when fully open, is larger than the at least one further opening, and
- wherein the free end of the flexible tube comprises a closure or seal for at least one of:
    - closing the free end of the flexible tube; and
    - sealing around an instrument inserted through said free end.

20. The tissue receiving bag according to claim 19, where the closure or seal is comprised by the bag prior to insertion of the bag into a human or animal body.

21. The tissue receiving bag according to claim 19, wherein the seal or closure is provided such that the free end of the tube can be closed off by the seal or closure or made to seal around an instrument inserted through said free end while said free end with the closure or seal is outside a human or animal body when the flexible tube extends through an incision into the human or animal body.

* * * * *